US008079971B2

(12) United States Patent
Becerra

(10) Patent No.: US 8,079,971 B2
(45) Date of Patent: Dec. 20, 2011

(54) SPINAL MOBILIZATION TREATMENT SYSTEM WITH MULTI-DIMENSIONAL FORCE APPLICATION

(75) Inventor: Carlos Becerra, Atlanta, GA (US)

(73) Assignee: North American Medical Corporation, Marietta, GA (US)

( * ) Notice: Subject to any disclaimer, the term of this patent is extended or adjusted under 35 U.S.C. 154(b) by 273 days.

(21) Appl. No.: 12/474,462

(22) Filed: May 29, 2009

(65) Prior Publication Data

US 2009/0299247 A1 Dec. 3, 2009

Related U.S. Application Data

(60) Provisional application No. 61/056,863, filed on May 29, 2008.

(51) Int. Cl.
*A61F 5/00* (2006.01)
*A63B 26/00* (2006.01)

(52) U.S. Cl. .......................... 602/32; 606/239; 482/142

(58) Field of Classification Search .......... 602/1, 32–40; 482/79–80, 91–92, 131, 907, 122–126; 601/40, 601/27, 29, 33
See application file for complete search history.

(56) References Cited

U.S. PATENT DOCUMENTS

| | | | | |
|---|---|---|---|---|
| 4,930,524 A * | 6/1990 | van Zuilichem | .............. | 128/876 |
| 6,615,676 B2 * | 9/2003 | Rankin | ...................... | 73/862.41 |
| 7,297,091 B2 * | 11/2007 | Nushart | .......................... | 482/79 |
| 2006/0142683 A1 * | 6/2006 | Johnson et al. | ................. | 602/32 |
| 2008/0188780 A1 * | 8/2008 | Becerra | ........................... | 601/49 |

* cited by examiner

*Primary Examiner* — Patricia Bianco
*Assistant Examiner* — Tarla Patel
(74) *Attorney, Agent, or Firm* — Bryan W. Bockhop; Bockhop & Associates, LLC

(57) ABSTRACT

A spinal treatment system for treating a spinal region of a patient's back includes a harness configured to be coupled to a preselected location on the patient. A force transfer member is coupled to the harness and is configured to transfer force to the harness. A vibrational movement head is controlled by a computer and is configured to apply a preselected laterally vibrating force to the force application member extending therefrom. A vertical displacement member is coupled to the computer and is configured to move the vibrational movement head to a preselected vertical displacement relative to the patient.

14 Claims, 2 Drawing Sheets

SPINAL MOBILIZATION TREATMENT SYSTEM WITH MULTI-DIMENSIONAL FORCE APPLICATION

CROSS-REFERENCE TO RELATED APPLICATION(S)

This application claims the benefit of U.S. Provisional Patent Application Ser. No. 61/056,863, filed May 29, 2008, the entirety of which is hereby incorporated herein by reference.

BACKGROUND OF THE INVENTION

1. Field of the Invention

The present invention relates to medical devices and, more specifically, to a device for applying selected forces to a patient's spine.

2. Description of the Prior Art

Spinal treatment devices treat lower back pain by applying a force to selected vertebrae of a patient. Existing spinal devices apply either a static force on the patient or a simple cyclical force to the patient. The use of oscillations allows the patient to relax while the force is being applied, thereby facilitating the treatment. The simple cyclical patterns, however, tend to relax only certain muscles in the spinal area and, thus, fail to achieve complete relaxation quickly. Complete relaxation makes spinal rehabilitation more effective. Also, there is evidence that certain vibrations frequencies stimulate tissue regeneration and bone growth.

In certain situations, applying a specific vibration frequency to a specific location on the patient's spine is beneficial. Existing systems generally apply a vibration to a harness, but do not target specific locations for the vibrations.

Therefore, there is a need for a system that is configured to apply vibrations of a specific frequency to a specific location on the patient's spine, while also applying a predetermined force to the patient's spine.

SUMMARY OF THE INVENTION

The disadvantages of the prior art are overcome by the present invention which, in one aspect, is a spinal treatment system for treating a spinal region of a patient's back that includes a harness, a force transfer member, a computer, a vibrational movement head and a vertical displacement member. The harness is configured to be coupled to a preselected location on the patient. The force transfer member is coupled to the harness and is configured to transfer force to the harness. The vibrational movement head is controlled by the computer and is configured to apply a preselected laterally vibrating force to the force application member extending therefrom. The vertical displacement member is coupled to the computer and is configured to move the vibrational movement head to a preselected vertical displacement relative to the patient.

In another aspect, the invention is a spinal treatment system for treating a spinal region of a patient's back. A horizontal treatment bed is configured to support the patient during spinal treatment. A selected one of a metal rod or a steel cable is coupled to the harness and configured to transfer force to the harness while the patient is reclined on the horizontal treatment bed. A harness is coupled to a preselected location on the patient. The harness includes a coupler for coupling the selected one of a metal rod or a steel cable to the harness. The vibrational movement head is controlled by a computer and is configured to apply a preselected laterally vibrating force to the selected one of a metal rod or a steel cable extending therefrom. The vertical displacement member is disposed adjacent to an end of the treatment bed and is coupled to and is controlled by the computer. The vertical displacement member is configured to move the vibrational movement head to a preselected vertical displacement relative to the patient.

In yet another aspect, the invention is a harness for use with a spinal decompression treatment system. The harness includes a harness member, including an adjustable girdle, that is configured to be disposed snugly about a patient. An amplifier is configured to amplify a vibration signal. A transducer is disposed so as to be placed adjacent to the patient's back. The transducer is configured to receive an amplified vibration signal from the amplifier and to generate mechanical vibrations corresponding thereto.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
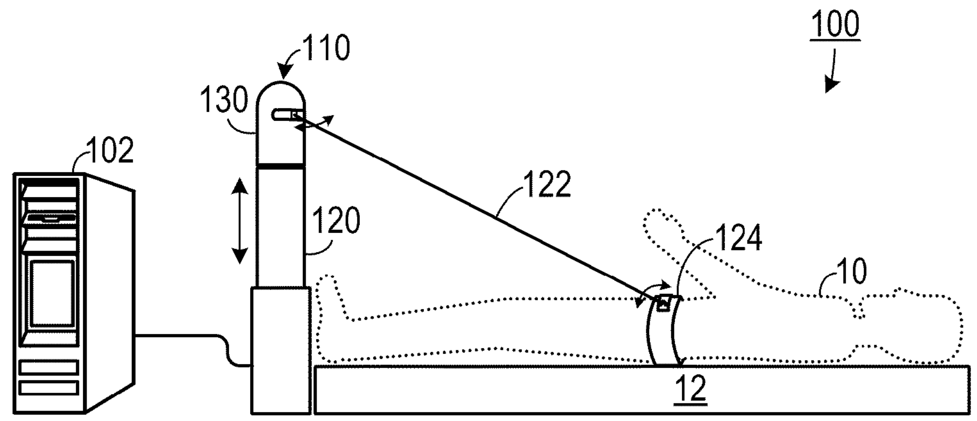
FIG. 1 is an elevational view of a spinal treatment structure according to one embodiment of the invention.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIG. 1, one embodiment of the invention is a spinal treatment system 100 that includes a treatment bed 12 upon which a patient 10 reclines and a spinal force device 110 that includes a mechanism 120 for adjusting a vertical displacement of a vibrational movement head 130, thereby adjusting the angle at which force is applied to the patient 10 through a force transfer member, such as a metal rod 122 or a steel cable. (The mechanism, for example, could include a mechanical or a hydraulic lift.) The rod 122 applies force to a harness 124 that transfers the force to the patient 10. The vibrational device 130 is controlled by a computer 110, which controls the vibrational movement head 130 to cause it to apply a selected vibrational profile to the rod 122, while applying a preselected tension to the rod 122 at a preselected angle to the patient 10.

The vibrational movement head 130 and the mechanism 120 for adjusting a vertical displacement thereof are controlled by a computer 102. The computer is programmable to cause the vibrational movement head 130 and the mechanism 120 to apply a preselected profile of tensions, vibrations and tensile force to the patient's spine for a desired amount of time, according to a prescription devised by a back treatment professional.

The rod 122 may be interchanged with rods of different diameters so that the resonant frequency of the rod 122 will correspond to the frequency of the vibrations being applied to the patient. Thus, the diameter of the rod 122 can be chosen to match the needs of the patient 10.

Figure 2:
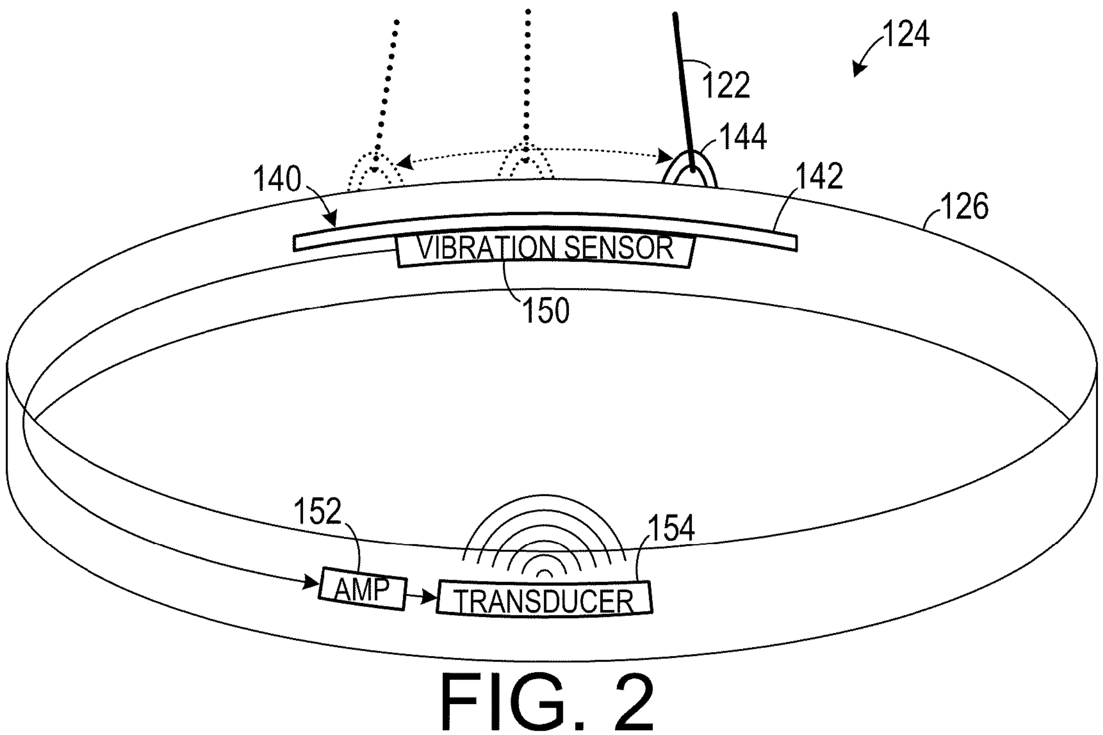
FIG. 2 is a schematic view of a harness that may be employed with the embodiment shown in FIG. 1.

As shown in FIG. 2, the harness 124 includes a harness member such as an adjustable belt-like girdle structure 126 configured to engage a preselected location on he patient's body. The harness 124 includes a selectively-positional attachment structure 140 that allows coupling of the harness 124 to the rod 122 at one of several different positions. The selectively-positional attachment structure 140 includes a coupler 144 that attaches the rod 122 and a track 142 along which the coupler 144 may be positioned.

The harness 124 also includes a vibration sensor 150 positioned adjacent to the track 142 and configured to sense vibrations transmitted from the rod 122. An amplifier 152 amplifies the vibrations sensed by the vibration sensor 150 and a transducer 154 (such as a speaker or other vibration generator) regenerates the vibrations and applies them to a selected zone on the patient's back.

Figure 3A:
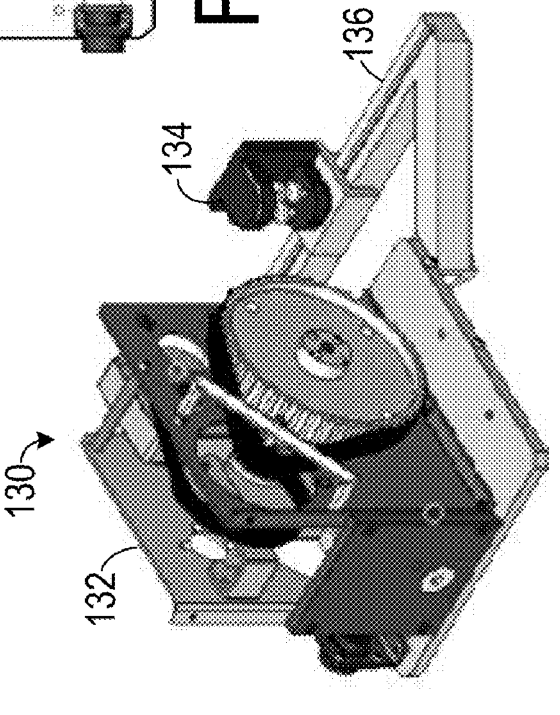
FIGS. 3A-C are three elevational views of a vibrational head may be employed with the embodiment shown in FIG. 1.
Figure 3B:
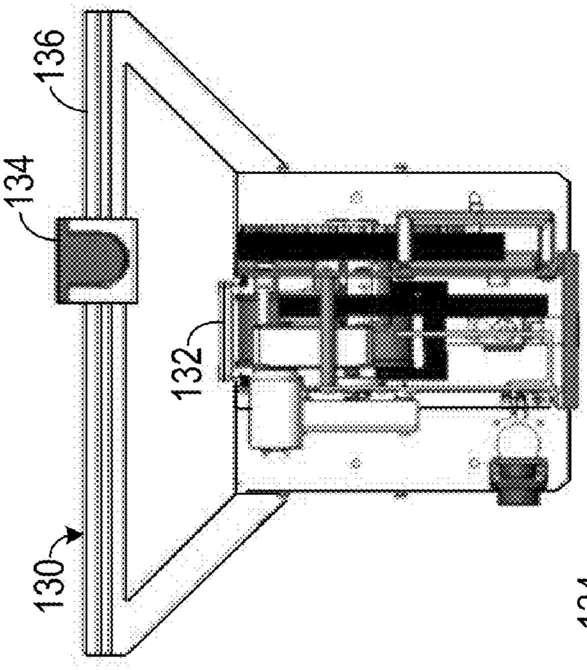
Figure 3C:
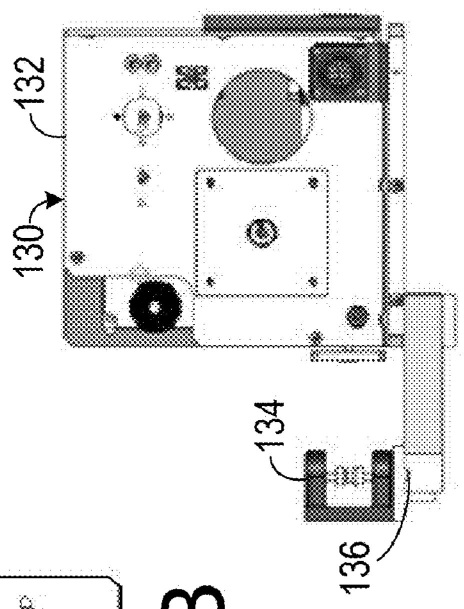

As shown in FIGS. 3A-3C, the vibrational device head 130 includes an actuator 132 for applying force and vibrations to the rod. The rod is engaged to an attachment structure 134, which is mounted on a track 136. The attachment structure 134 may be selectively positioned on the track 136 so that force may be applied to the rod at a specific angle.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A spinal treatment system for treating a spinal region of a patient's back, comprising:
- a. a harness configured to be coupled to a preselected location on the patient;
- b. a force transfer member coupled to the harness and configured to transfer force to the harness;
- c. a computer;
- d. a vibrational movement head controlled by the computer and configured to apply a preselected laterally vibrating force to the force application member extending therefrom, the vibrational movement head including:
  - i. an attachment structure coupled to the force transfer member;
  - ii. a lateral track coupled to the attachment structure and configured to allow selective lateral movement of the attachment structure along the lateral track; and
  - iii. an actuator, responsive to the computer, configured to move the attachment structure to at least one preselected position along the track and configured to apply a preselected amount of tensile force to the force transfer member; and
- e. a vertical displacement member coupled to the computer and configured to move the vibrational movement head to a preselected vertical displacement relative to the patient.

2. The spinal treatment system of claim 1, wherein the harness comprises:
- a. a harness member configured to be disposed snugly about a patient;
- b. a coupler for coupling the force transfer member to the harness member;
- c. a vibration sensor disposed adjacent to the coupler and configured to sense a vibration from the coupler;
- d. an amplifier configured to amplify a vibration signal received from the vibration sensor; and
- e. a transducer disposed so as to be placed adjacent to the patient's back, the transducer configured to receive an amplified vibration signal from the amplifier and to generate mechanical vibrations corresponding thereto.

3. The spinal treatment system of claim 2, wherein the harness member comprises an adjustable girdle.

4. The spinal treatment system of claim 1, wherein the force transfer member comprises a metal rod.

5. The spinal treatment system of claim 1, wherein the force transfer member comprises a steel cable.

6. The spinal treatment system of claim 1, further comprising a horizontal treatment bed configured to support the patient during spinal treatment.

7. A spinal treatment system for treating a spinal region of a patient's back, comprising:
- a. a horizontal treatment bed configured to support the patient during spinal treatment;
- b. a selected one of a metal rod or a steel cable coupled to the harness and configured to transfer force to the harness while the patient is reclined on the horizontal treatment bed;
- c. a harness configured to be coupled to a preselected location on the patient, the harness including a coupler for coupling the selected one of a metal rod or a steel cable to the harness, the harness including:
  - i. a vibration sensor disposed adjacent to the coupler and configured to sense a vibration from the coupler;
  - ii. an amplifier configured to amplify a vibration signal received from the vibration sensor; and
  - iii. a transducer disposed so as to be placed adjacent to the patient's back, the transducer configured to receive an amplified vibration signal from the amplifier and to generate mechanical vibrations corresponding thereto;
- d. a computer;
- e. a vibrational movement head controlled by the computer and configured to apply a preselected laterally vibrating force to the selected one of a metal rod or a steel cable extending therefrom; and
- f. a vertical displacement member disposed adjacent to an end of the treatment bed and coupled to the computer, the vertical displacement member configured to move the vibrational movement head to a preselected vertical displacement relative to the patient.

8. The spinal treatment system of claim 7, wherein the harness comprises a track to which the coupler is engaged so that the coupler is movable laterally with respect to the harness.

9. The spinal treatment system of claim 7, wherein the vibrational movement head comprises:
- a. an attachment structure coupled to the selected one of a metal rod or a steel cable;
- b. a lateral track coupled to the attachment structure and configured to allow selective lateral movement of the attachment structure along the lateral track; and
- c. an actuator, responsive to the computer, configured to move the attachment structure to at least one preselected position along the track and configured to apply a preselected amount of tensile force to the selected one of a metal rod or a steel cable.

10. A harness for use with a spinal decompression treatment system, comprising:

a. a harness member, including an adjustable girdle, configured to be disposed snugly about a patient;

b. an amplifier configured to amplify a vibration signal; and c. a transducer disposed so as to be placed adjacent to the patient's back, the transducer configured to receive an amplified vibration signal from the amplifier and to generate mechanical vibrations corresponding thereto.

11. The harness of claim 10, further comprising:

a. a coupler for coupling a force transfer member to the harness member; and b. a vibration sensor disposed adjacent to the coupler and configured to sense a vibration from the coupler.

12. The harness of claim 11, wherein the harness member includes a track to which the coupler is engaged so that the coupler is laterally moveable with respect to the harness.

13. The harness of claim 11, wherein the coupler comprises a metal buckle attached centrally to the harness member.

14. The harness of claim 10, wherein the force transfer member is coupled to a spinal decompression system.

* * * * *